(12) United States Patent
Reggiani et al.

(10) Patent No.: US 8,795,220 B2
(45) Date of Patent: Aug. 5, 2014

(54) BLOOD PROCESSING UNIT WITH CIRCUMFERENTIAL BLOOD FLOW

(75) Inventors: Stefano Reggiani, Medolla (IT); Gianfranco Beniamino Fiore, Milan (IT); Alberto Giri, Mirandola (IT); Alberto Redaelli, Milan (IT); Claudio Silvestri, Quarantoli Mirandola (IT); Gabriele Tommasi, Cavezzo (IT)

(73) Assignees: Politecnico di Milano, Milan (IT); Sorin Group Italia S.r.l., Milan (IT)

( * ) Notice: Subject to any disclaimer, the term of this patent is extended or adjusted under 35 U.S.C. 154(b) by 64 days.

(21) Appl. No.: 12/947,171

(22) Filed: Nov. 16, 2010

(65) Prior Publication Data

US 2012/0121463 A1 May 17, 2012

(30) Foreign Application Priority Data

Nov. 15, 2010 (EP) ..................... 10191140

(51) Int. Cl.
  *A61M 1/36* (2006.01)
  *A61M 1/16* (2006.01)
  *B01D 63/02* (2006.01)

(52) U.S. Cl.
  CPC ........... *A61M 1/1698* (2013.01); *A61M 1/3627* (2013.01); *A61M 1/3666* (2013.01); *B01D 63/02* (2013.01); *A61M 2206/10* (2013.01); *A61M 2206/14* (2013.01); *A61M 2206/16* (2013.01); *A61M 2206/18* (2013.01); *A61M 2206/20* (2013.01); *B01D 2313/38* (2013.01); *B01D 2313/19* (2013.01); *B01D 2313/32* (2013.01); *B01D 2313/08* (2013.01); *Y10S 128/03* (2013.01); *Y10S 261/28* (2013.01)
  USPC ....... 604/6.14; 604/5.01; 604/6.13; 604/4.01; 422/44; 128/DIG. 3; 261/DIG. 28

(58) Field of Classification Search
  CPC ........... A61M 1/1698; A61M 1/3627; A61M 2205/366; A61M 2206/10; A61M 2206/12; A61M 2206/14; A61M 2206/16; A61M 2206/18; A61M 2206/20; A61M 1/3666; B01D 63/02; B01D 2313/38; B01D 2313/12; B01D 2313/125; B01D 2313/19; B01D 2313/20; B01D 2313/32; B01D 2313/08; Y10S 128/03; Y10S 261/28
  USPC ................ 604/4.01, 5.01, 6.11, 6.13, 6.14, 7; 422/44, 45, 46
  See application file for complete search history.

(56) References Cited

U.S. PATENT DOCUMENTS 3,957,648 A * 5/1976 Roget et al. .............. 210/321.88
4,038,190 A   7/1977 Baudet et al.
(Continued)

FOREIGN PATENT DOCUMENTS

EP   0312125 A1   4/1989
EP   0582959 A1   2/1994
(Continued)

OTHER PUBLICATIONS

European Search Report issued in EP Application No. 10161451, dated Sep. 28, 2010, 5 pages.

(Continued)

*Primary Examiner* — Adam Marcetich
(74) *Attorney, Agent, or Firm* — Faegre Baker Daniels LLP

(57) ABSTRACT

A blood processing apparatus may include a heat exchanger and a gas exchanger. At least one of the heat exchanger and the gas exchanger may be configured to provide a circumferential blood flow through the heat exchanger and/or gas exchanger.

13 Claims, 11 Drawing Sheets

(56) References Cited

U.S. PATENT DOCUMENTS

| | | | |
|---|---|---|---|
| 4,229,305 A * | 10/1980 | Fecondini et al. | 210/321.83 |
| 4,597,868 A | 7/1986 | Watanabe | |
| 4,639,353 A * | 1/1987 | Takemura et al. | 422/46 |
| 4,902,476 A | 2/1990 | Gordon et al. | |
| 5,169,530 A * | 12/1992 | Schucker et al. | 210/321.81 |
| 5,192,439 A | 3/1993 | Roth et al. | |
| 5,192,499 A | 3/1993 | Sakai et al. | |
| 5,270,004 A * | 12/1993 | Cosentino et al. | 422/46 |
| 5,316,724 A * | 5/1994 | Mathewson et al. | 422/48 |
| 5,338,512 A * | 8/1994 | Mathewson et al. | 422/46 |
| 5,514,095 A | 5/1996 | Brightbill et al. | |
| 5,578,267 A | 11/1996 | Cosentino et al. | |
| 5,674,452 A * | 10/1997 | Carson et al. | 422/46 |
| 5,733,398 A * | 3/1998 | Carson et al. | 156/69 |
| 5,762,868 A * | 6/1998 | Leonard | 422/46 |
| 5,762,869 A * | 6/1998 | White et al. | 422/48 |
| 5,817,278 A | 10/1998 | Fini et al. | |
| 5,817,279 A * | 10/1998 | Eilers et al. | 422/46 |
| 5,830,370 A | 11/1998 | Maloney, Jr. et al. | |
| RE36,774 E | 7/2000 | Cosentino et al. | |
| 6,105,664 A * | 8/2000 | Gillbrand et al. | 165/119 |
| 6,113,782 A | 9/2000 | Leonard | |
| 6,241,945 B1 | 6/2001 | Owen | |
| 6,454,999 B1 * | 9/2002 | Farhangnia et al. | 422/45 |
| 6,755,894 B2 * | 6/2004 | Bikson et al. | 95/52 |
| 6,960,322 B2 | 11/2005 | Stringer et al. | |
| 8,318,092 B2 | 11/2012 | Reggiani et al. | |
| 8,388,566 B2 | 3/2013 | Reggiani et al. | |
| 8,394,049 B2 | 3/2013 | Reggiani et al. | |
| 2002/0039543 A1 * | 4/2002 | Ikeda et al. | 422/48 |
| 2003/0080047 A1 * | 5/2003 | Watkins et al. | 210/456 |
| 2004/0175292 A1 | 9/2004 | Ghellil et al. | |
| 2004/0251011 A1 * | 12/2004 | Kudo | 165/172 |
| 2007/0107884 A1 | 5/2007 | Sirkar et al. | |
| 2007/0166190 A1 * | 7/2007 | Ogihara et al. | 422/45 |
| 2007/0231203 A1 * | 10/2007 | Mizoguchi et al. | 422/45 |
| 2008/0234623 A1 * | 9/2008 | Strauss et al. | 604/6.11 |
| 2010/0269342 A1 | 10/2010 | Carpenter et al. | |
| 2010/0272606 A1 * | 10/2010 | Carpenter et al. | 422/46 |
| 2010/0272607 A1 | 10/2010 | Carpenter et al. | |
| 2011/0268608 A1 | 11/2011 | Reggiani et al. | |
| 2011/0268609 A1 | 11/2011 | Reggiani et al. | |
| 2012/0046594 A1 | 2/2012 | Reggiani et al. | |
| 2012/0294761 A1 | 11/2012 | Reggiani et al. | |
| 2013/0142695 A1 | 6/2013 | Reggiani et al. | |
| 2013/0142696 A1 | 6/2013 | Reggiani et al. | |

FOREIGN PATENT DOCUMENTS

| | | |
|---|---|---|
| EP | 0895786 A1 | 2/1999 |
| EP | 1108462 A2 | 6/2001 |
| EP | 1180374 A1 | 2/2002 |
| EP | 1371381 A1 | 12/2003 |
| EP | 1834656 B1 | 9/2007 |
| WO | WO9716213 A2 | 5/1997 |
| WO | WO9719714 A1 | 6/1997 |
| WO | WO9733636 A1 | 9/1997 |

OTHER PUBLICATIONS

European Search Report issued in EP Application No. 10173436, dated Feb. 14, 2011, 7 pages.

European Search Report issued in EP Application No. 10186550, dated Jan. 27, 2011, 7 pages.

International Search Report issued in PCT/IB2011/054725, mailed Feb. 9, 2012, 12 pages.

International Search Report and Written Opinion issued in PCT/IB2012/052424, mailed Oct. 24, 2012, 17 pages.

* cited by examiner

BLOOD PROCESSING UNIT WITH CIRCUMFERENTIAL BLOOD FLOW

CROSS-REFERENCE TO RELATED APPLICATION

This application claims priority to European patent application EP10191140.2, filed Nov. 15, 2010, under 35 U.S.C. §119, which is herein incorporated by reference in its entirety. This application is related to U.S. patent application Ser. No. 12/860,062, filed Aug. 20, 2010, entitled "Blood Processing Unit with Modified Flow Path," which is hereby incorporated by reference in its entirety.

BACKGROUND

The disclosure pertains generally to blood processing units used in blood perfusion systems. Blood perfusion entails encouraging blood through the vessels of the body. For such purposes, blood perfusion systems typically entail the use of one or more pumps in an extracorporeal circuit that is interconnected with the vascular system of a patient. Cardiopulmonary bypass surgery typically requires a perfusion system that provides for the temporary cessation of the heart to create a still operating field by replacing the function of the heart and lungs. Such isolation allows for the surgical correction of vascular stenosis, valvular disorders, and congenital heart defects. In perfusion systems used for cardiopulmonary bypass surgery, an extracorporeal blood circuit is established that includes at least one pump and an oxygenation device to replace the functions of the heart and lungs.

More specifically, in cardiopulmonary bypass procedures oxygen-poor blood, i.e., venous blood, is gravity-drained or vacuum suctioned from a large vein entering the heart or other veins in the body (e.g., femoral) and is transferred through a venous line in the extracorporeal circuit. The venous blood is pumped to an oxygenator that provides for oxygen transfer to the blood. Oxygen may be introduced into the blood by transfer across a membrane or, less frequently, by bubbling oxygen through the blood. Concurrently, carbon dioxide is removed across the membrane. The oxygenated blood is filtered and then returned through an arterial line to the aorta, femoral artery, or other artery.

SUMMARY

Example 1 is a blood processing apparatus including a housing having a blood inlet and a blood outlet, the blood inlet extending into an interior of the housing. A core is arranged coaxially within the housing, the core having a core interior in fluid communication with the blood inlet, the core including an outer surface and an elongate core aperture formed within the outer surface and extending generally parallel to a core longitudinal axis, the elongate core aperture configured to permit blood to exit from the core interior. Heat exchanger hollow fibers are disposed about the core such that a heat exchanger fluid may flow through the heat exchanger hollow fibers and blood passing from the elongate core aperture may flow across the heat exchanger hollow fibers. A cylindrical shell is arranged coaxially about the heat exchanger hollow fibers, the cylindrical shell including an elongate shell aperture configured to permit blood to exit from the cylindrical shell. Gas exchanger hollow fibers are disposed about the inner cylindrical shell such that gases may flow through the gas exchange hollow fibers and blood passing from the elongate shell aperture may flow across the gas exchanger hollow fibers and towards the blood outlet. The shell aperture is disposed at a location substantially diametrically opposite the location of the core aperture, such that blood flows across the heat exchanger hollow fibers is substantially circumferential.

Example 2 is the blood processing apparatus of Example 1, wherein the cylindrical shell further includes a plurality of lobes configures to impart a radial flow component to the blood.

Example 3 is the blood processing apparatus of any of Examples 1-2, further comprising an elongate collection space disposed between the gas exchanger hollow fibers and the housing, the collection space diametrically opposed to the elongate shell aperture and in fluid communication with the blood outlet.

Example 4 is the blood processing apparatus of any of Examples 1-3, wherein the shell aperture comprises a radially disposed aperture disposed near an end of the cylindrical shell opposite that of the blood inlet such that blood exiting the radially disposed aperture flows over the gas exchanger hollow fibers in a longitudinal direction.

Example 5 is the blood processing apparatus of any of Examples 1-4, wherein the housing defines an annular space configured to collect blood passing over the gas exchanger hollow fibers and direct the blood towards the blood outlet.

Example 6 is the blood processing apparatus of any of Examples 1-5, wherein the core includes a pair of elongate core apertures disposed generally parallel to each other and in close proximity to each other within the outer surface such that blood exiting a first of the pair elongate core apertures flows in a first circumferential direction and blood exiting a second of the pair of elongate core apertures flows in a second circumferential direction generally opposite the first circumferential direction.

Example 7 is the blood processing apparatus of any of Examples 1-6, wherein the outer surface of the core comprises a plurality of longitudinally extending core ribs that are configured to impart a radial component to blood flow around the heat exchanger core.

Example 8 is the blood processing apparatus of any of Examples 1-7, wherein the cylindrical shell has an inner surface and a plurality of longitudinally extending shell ribs on the inner surface of the cylindrical shell that are configured to impart a radial component to blood flow around the core.

Example 9 is the blood processing apparatus of any of Examples 1-8, wherein the outer surface of the heat exchanger core further comprises a plurality of transverse ribs that are configured to provide a space between the heat exchanger core and the heat exchanger hollow fibers.

Example 10 is the blood processing apparatus of claim any of Examples 1-9, wherein the cylindrical shell comprises an elongate shell aperture disposed diametrically opposed to the pair of elongate core apertures.

Example 11 is a blood processing apparatus including an outer housing having a blood inlet and a blood outlet. A heat exchanger core is arranged within the housing and having a core interior in fluid communication with the blood inlet, the heat exchanger core including an outer surface and an elongate channel formed through the outer surface such that blood may exit from the core interior with a generally circumferential flow configuration. Heat exchanger hollow fibers are disposed about the heat exchanger core such that a heat exchanger fluid may flow through the heat exchanger hollow fibers and blood exiting from the core aperture may flow across the heat exchanger hollow fibers. A cylindrical shell is arranged coaxially about the heat exchanger hollow fibers, the cylindrical shell including an elongate channel formed within an inner surface of the shell, at a circumferential location generally opposite a location of the elongate channel, and a radially disposed shell aperture disposed near an end opposite the blood outlet, wherein the elongate channel and the shell aperture are in fluid communication, such that blood passing over the heat exchanger hollow fibers flows into the elongate channel and exits the cylindrical shell through the shell aperture. Gas exchanger hollow fibers are disposed about the cylindrical shell such that gases may flow through the gas exchange hollow fibers and blood passing from the cylindrical shell may flow across the gas exchanger hollow fibers towards the blood outlet in a longitudinal flow path.

Example 12 is the blood processing apparatus of Example 11, wherein the inner surface of the cylindrical shell further includes a plurality of lobes configures to impart a radial flow component to the blood.

Example 13 is the blood processing apparatus of Example 11 or 12, wherein the heat exchanger core includes a pair of elongate core apertures disposed generally parallel to each other and in close proximity to each other within the outer surface such that blood exiting a first of the pair elongate core apertures flows in a first circumferential direction and blood exiting a second of the pair of elongate core apertures flows in a second circumferential direction generally opposite the first circumferential direction.

Example 14 is the blood processing apparatus of any of Examples 11-13, wherein the outer surface of the core comprises a plurality of longitudinally extending core ribs that are configured to impart a radial component to blood flow around the heat exchanger core.

Example 15 is the blood processing apparatus of any of Examples 11-14, wherein the cylindrical shell has an inner surface and a plurality of longitudinally extending shell ribs on the inner surface of the cylindrical shell that are configured to impart a radial component to blood flow around the core.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

The disclosure pertains to a blood processing apparatus that, according to various exemplary embodiments, includes one or more of a heat exchanger and a gas exchanger (also commonly referred to as an oxygenator). In some embodiments, the term oxygenator may be used to refer to an integrated structure that combines a heat exchanger and a gas exchanger in a unitary device. In various embodiments, for example, the heat exchanger and gas exchanger are disposed in a concentric fashion with one component located inside of the other component. According to other embodiments, the heat exchanger and gas exchanger are structurally distinct structures operably coupled to each other. In some embodiments, an oxygenator may be used in an extracorporeal blood circuit. An extracorporeal blood circuit, such as may be used in a bypass procedure, may include several different elements such as a heart-lung machine, a blood reservoir, as well as an oxygenator.

Figure 1:
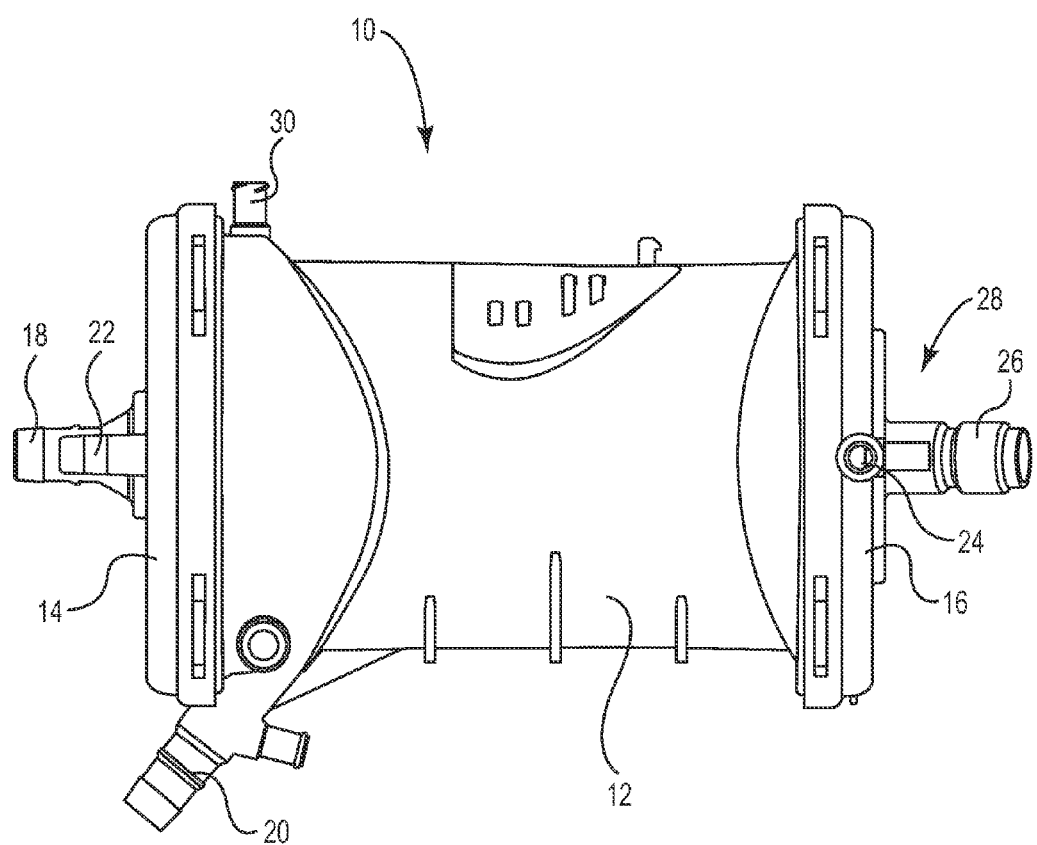
FIG. 1 is a schematic illustration of a blood processing apparatus in accordance with an embodiment of the invention.

FIG. 1 is a schematic illustration of a blood processing apparatus or oxygenator 10. While the internal components are not visible in this illustration, the oxygenator 10 may include one or more of a heat exchanger and a gas exchanger. According to some embodiments, the heat exchanger and the gas exchanger are integrated into a single structure that forms an oxygenator housing. The oxygenator 10 includes a housing 12, a first end cap 14 that is secured to the housing 12 and a second end cap 16 that is secured to the housing 12. In some embodiments, the housing 12 may include other structure that enables attachment of the housing 12 to other devices. While the housing 12 is illustrated as largely cylindrical in shape, in some embodiments, the housing 12 may have a triangular, rectangular or other parallelogram cross-sectional shape. Each of the heat exchanger and the gas exchanger may have generally the same sectional shape or each may have a different sectional shape. In some embodiments, the heat exchanger may be inside the gas exchanger while in other embodiments the gas exchanger may be located within the heat exchanger. In some embodiments, the heat exchanger and the gas exchanger may be concentric.

In some embodiments, a blood inlet 18 extends into the housing 12 and a blood outlet 20 exits the housing 12. As noted, in some embodiments the blood processing apparatus 10 includes a gas exchanger and thus may include a gas inlet 22 and a gas outlet 24. In some embodiments, the blood processing apparatus 10 includes a heat exchanger and thus may include a heat exchanger fluid inlet 26 and a heat exchanger fluid outlet 28 that is behind (in the illustrated orientation) the heating fluid inlet 26. In some embodiments, the heat exchanger fluid inlet 26 may be disposed at one end of the housing 12 while the heat exchanger fluid outlet 28 may be disposed at an opposite end of the housing 12. In some embodiments, the blood processing apparatus 10 may include one or more purge ports 30 that may be used for purging air bubbles from the interior of the blood processing apparatus 10.

The positions of the inlets, outlets and purge port are merely illustrative, as other arrangements and configurations are contemplated. The purge port may include a valve or a threaded cap. The purge port operates to permit gases (e.g., air bubbles) that exit the blood to be vented or aspirated and removed from the blood processing apparatus 10.

Figure 2:
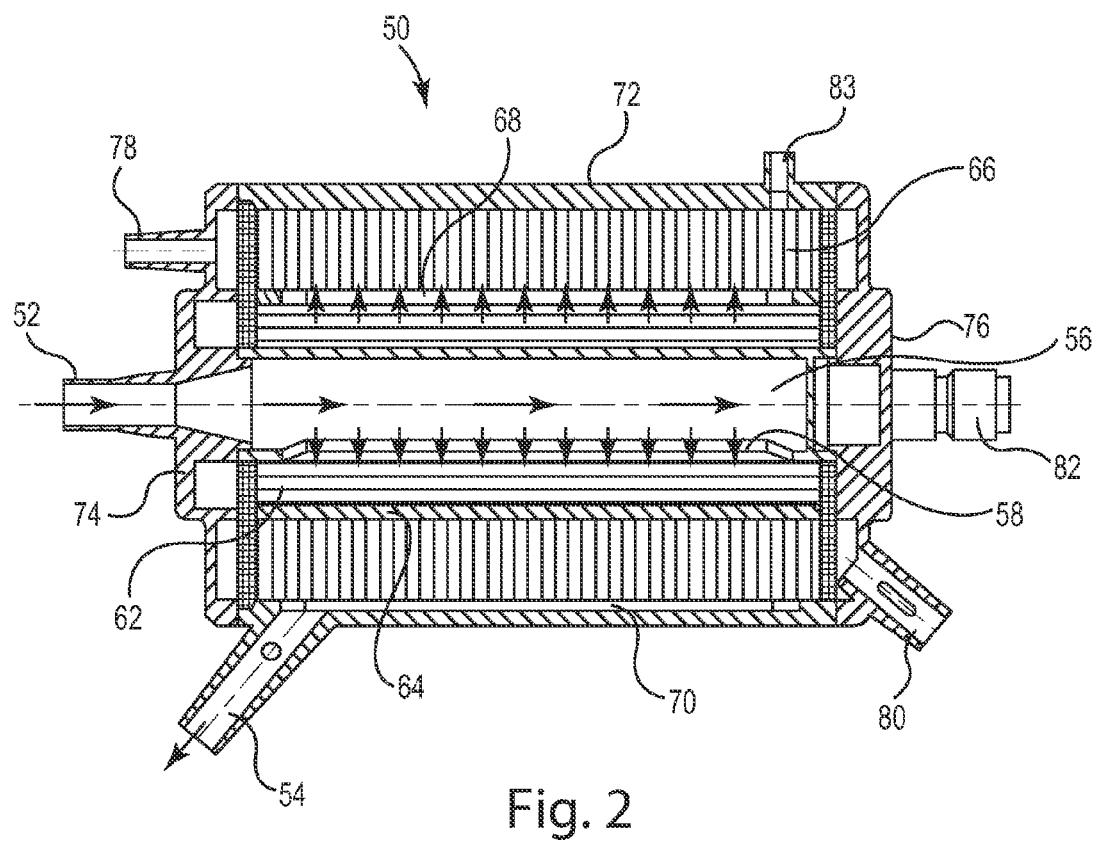
FIG. 2 is a cross-sectional view of a blood processing apparatus in accordance with an embodiment of the invention.
Figure 3:
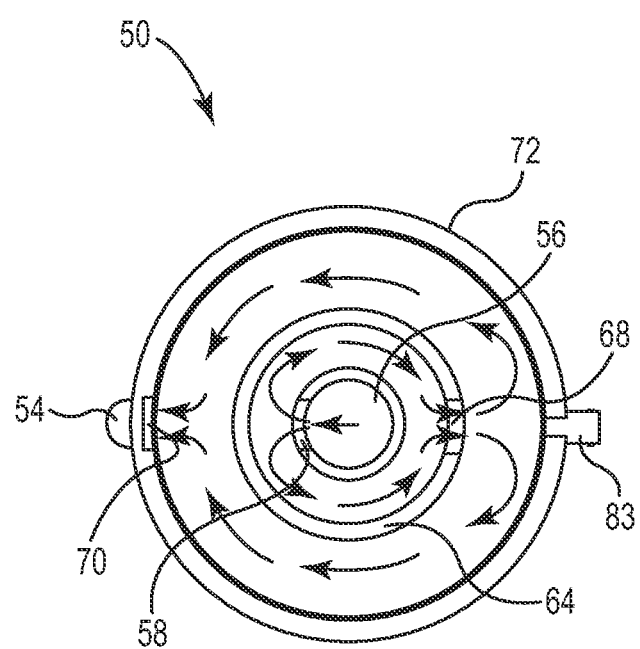
FIG. 3 is a cross-sectional view of an embodiment of a blood processing apparatus in accordance with an embodiment of the invention.
Figure 4:
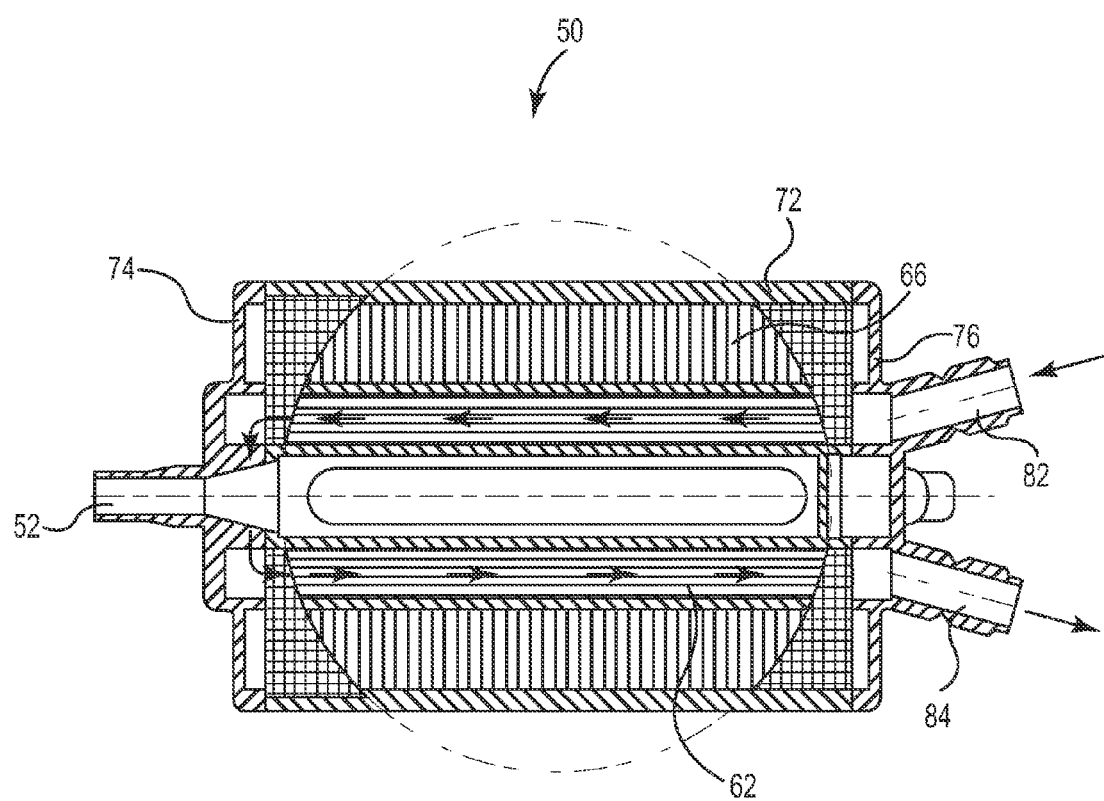
FIG. 4 is a cross-sectional view of an embodiment of a blood processing apparatus in accordance with an embodiment of the invention.
Figure 5:
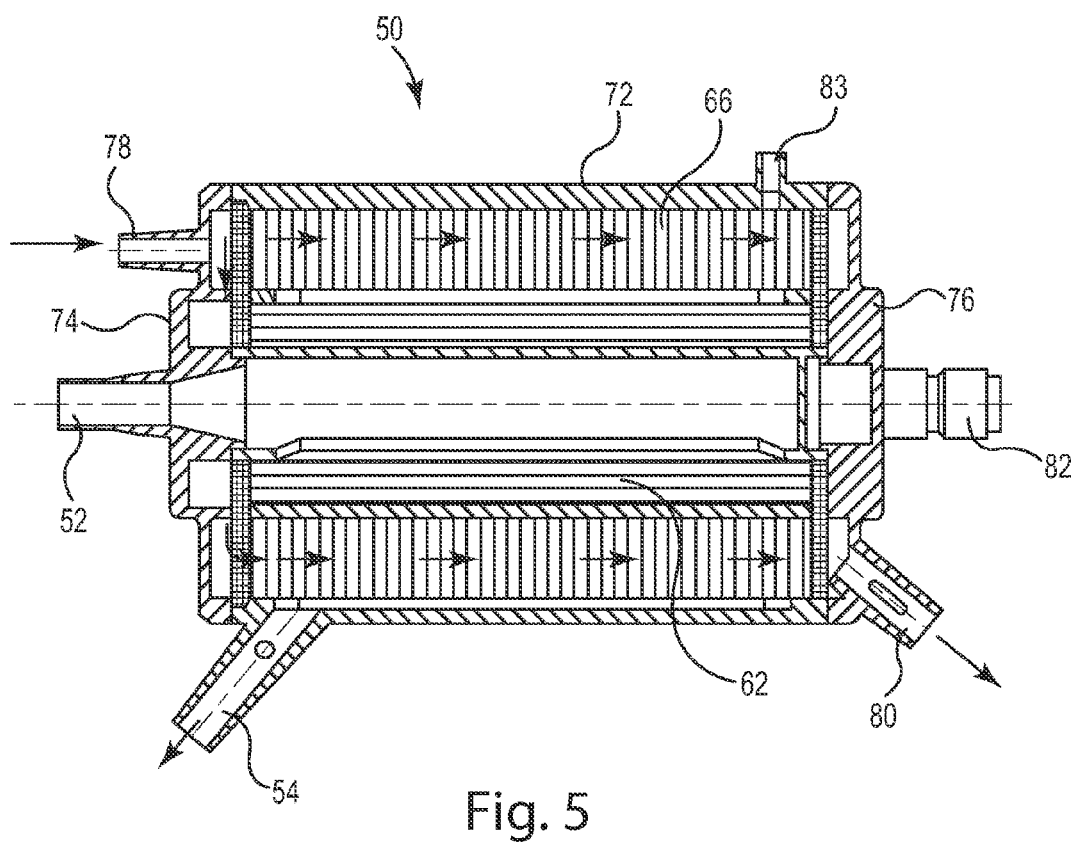
FIG. 5 is a cross-sectional view of an embodiment of a blood processing apparatus in accordance with an embodiment of the invention.

FIGS. 2-5 are views of a blood processing apparatus 50 in which blood flow through the heat exchanger is circumferential and blood flow through the gas exchanger is also circumferential. FIGS. 2 and 3 are cross-sectional views showing how blood flows through the blood processing apparatus 50 while FIGS. 4 and 5 show how heat exchanger fluid and exchanges gases, respectively, flow through the blood processing apparatus 50.

As seen in FIGS. 2 and 3, the blood processing apparatus 50 includes a blood inlet 52 and a blood outlet 54. The blood inlet 52 is fluidly coupled to a heat exchanger core 56 such that blood entering the blood inlet 52 flows into the heat exchanger core 56. In some embodiments, as illustrated, the heat exchanger core 56 includes an elongate core aperture 58 (e.g., a slot or channel extending at least partially along the longitudinal axis of the heat exchanger core 56) that allows blood to exit the heat exchanger core 56 and flow through a heat exchanger portion 62. In some embodiments, the elongate core aperture 58 permits blood to exit the core 56 in a generally radial direction, such that the blood may then flow through the heat exchanger portion 62 in a circumferential flow direction as illustrated in FIG. 2. According to some embodiments, the elongate core aperture extends longitudinally along substantially the entire effective length of the heat exchanger core 56. According to other embodiments, the elongate core aperture 58 is replaced with a series of shorter apertures. The core aperture 58 may extend from between about 1 and about 15 degrees about the circumference of the heat exchanger core 56. In one exemplary embodiment, the core aperture 58 extends about 5 degrees about the circumference.

As shown, the blood processing apparatus 50 includes an inner cylindrical shell 64 that delineates the heat exchanger portion 62 from a gas exchanger portion 66. In some embodiments, the cylindrical shell 64 includes an elongate shell aperture 68 that permits blood to flow into the gas exchanger portion 66. In some embodiments, the elongate shell aperture 68 permits blood to flow through the gas exchanger portion 66 in a circumferential fashion as seen in FIG. 3. The elongate shell aperture 68 may be disposed in the cylindrical shell 64 at a location substantially diametrically opposite the location of the core aperture 58. Once the blood has flown through the gas exchanger portion 66, the blood may collect in an elongate collection space 70 formed in the housing 12 before exiting the blood processing apparatus 10 through the blood outlet 54. According to other embodiments, the elongate shell aperture 68 is replaced with a series of shorter apertures.

In some embodiments, the circumferential blood flow through the heat exchanger portion 62 and through the gas exchanger portion 66 may be influenced by the relative location of internal structures within the blood processing apparatus 50. In some embodiments, as illustrated, the elongate shell aperture 68 is diametrically opposed (e.g., radially spaced about 180 degrees from) the elongate core aperture 58. Blood exits the elongate core aperture 58 and flows circumferentially through the heat exchanger portion 62 towards the elongate shell aperture 68. In some embodiments, the elongate collection space 70 is diametrically opposed to the elongate shell aperture 68 (and hence radially aligned with the elongate core aperture 58). Blood exits the elongate shell aperture 68 and flows circumferentially through the gas exchanger portion 66 towards the elongate collection space 70 before exiting the blood processing apparatus 50 through the blood outlet 54.

In some embodiments, the heat exchanger portion 62 includes a number of hollow fibers through which a heating fluid (e.g., water) can flow. The blood may flow around and past the hollow fibers and thus be suitably heated (or cooled). In some embodiments, the hollow fibers may be polymeric. In some cases, metallic fibers may be used. According to other embodiments, the heat exchanger portion 62 may instead include a metal bellows or other structure having a substantial surface area (e.g., fins) for facilitating heat transfer with the blood. In some embodiments, the hollow fibers may be formed of polyurethane, polyester, or any other suitable polymer or plastic material. According to various embodiments, the hollow fibers have an outer diameter of between about 0.2 and 1.0 millimeters or, more specifically, between about 0.25 and 0.5 millimeters. The hollow fibers may be woven into mats that can range, for example, from about 80 to about 200 millimeters in width. In some embodiments, the mats are arranged in a criss-cross configuration.

In some embodiments the gas exchanger portion 66 may include a number of microporous hollow fibers through which a gas such as oxygen may flow. The blood may flow around and past the hollow fibers. Due to concentration gradients, oxygen may diffuse through the microporous hollow fibers into the blood while carbon dioxide may diffuse into the hollow fibers and out of the blood. In some embodiments, the hollow fibers are made of polypropylene, polyester, or any other suitable polymer or plastic material. According to various embodiments, the hollow fibers have an outer diameter of about 0.38 millimeters. According to other embodiments, the microporous hollow fibers having a diameter of between about 0.2 and 1.0 millimeters, or more specifically, between about 0.25 and 0.5 millimeters. The hollow fibers may be woven into mats that can range, for example, from about 80 to about 200 millimeters in width. In some embodiments, the mats are in a criss-cross configuration.

In the embodiments shown in FIGS. 4 and 5, the blood processing apparatus 50 includes additional structural features. The blood processing apparatus 50 has a housing 72, a first end cap 74 and a second end cap 76. In some embodiments, the first end cap 74 may include a gas inlet 78 while the second end cap 76 may include a gas outlet 80. In some embodiments, the second end cap 76 may include a heat exchanger fluid inlet 82 and a heat exchanger fluid outlet 84 (see FIG. 4). In some embodiments, the housing 50 may include a purge port 83.

As shown in FIG. 4, heat exchanger fluid (such as heated or cooled water, saline or other suitable fluid) enters through the heat exchanger fluid inlet 82, passes through the heat exchanger hollow fibers within the heat exchanger portion 62, and then exits the blood processing apparatus 50 through the heat exchanger fluid outlet 84. In some embodiments, as illustrated, the heat exchanger fluid flows through the hollow fibers while the blood passes over and around the hollow fibers. In some embodiments, heated fluid is used to maintain and/or increase a temperature of the blood before it is returned or otherwise provided to the patient. In some embodiments, cooled fluid is used if, for example, there is a desire to cool the patient's body.

As shown in FIG. 5, gases (e.g., oxygen pass) enter through the gas inlet 78, passes through the microporous hollow fibers within the gas exchanger portion 66 and exits the blood processing apparatus 50 through the gas outlet 80. In some embodiments, the pressure or flow rate of oxygen through the blood processing apparatus 50 may be varied in order to achieve a desired diffusion rate of, for example, carbon dioxide diffusing out of the blood and oxygen diffusing into the blood. In some embodiments, as illustrated, the oxygen flows through the hollow fibers while the blood flows around and over the hollow fibers.

Figure 6:
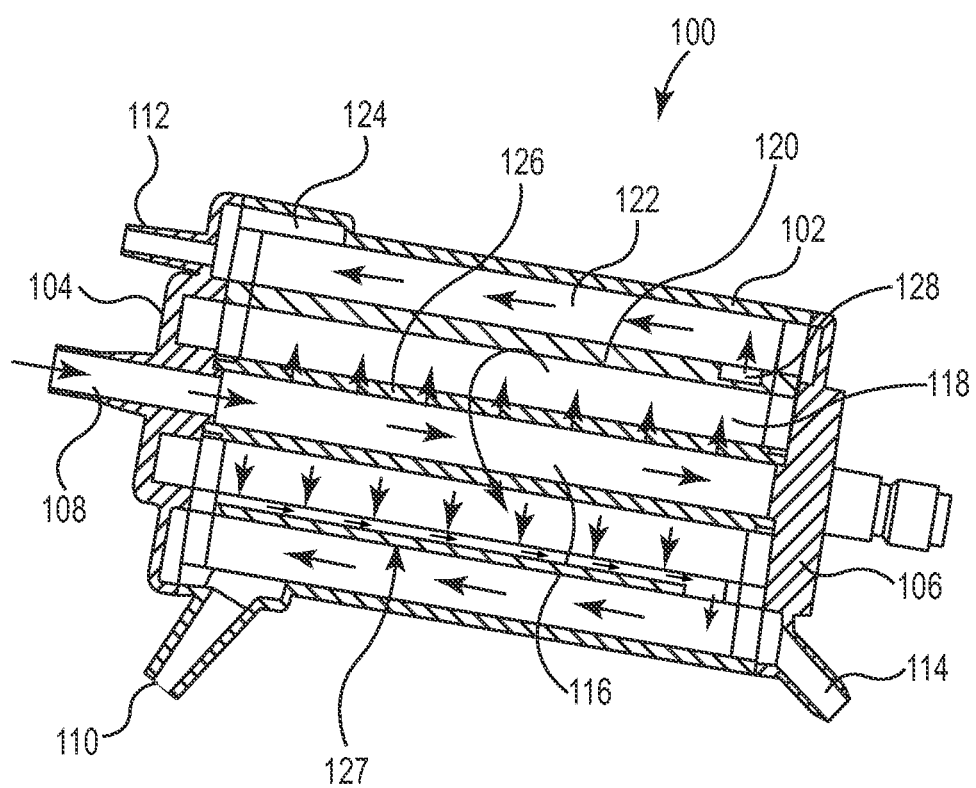
FIG. 6 is a cross-sectional view of an embodiment of a blood processing apparatus in accordance with an embodiment of the invention.

FIG. 6 is a cross-sectional view of a blood processing apparatus 100 in which blood flow through the heat exchanger portion is circumferential, while blood flow through the gas exchanger portion is longitudinal. As shown in FIG. 6, the blood processing apparatus 100 includes a housing 102, a first end cap 104 and a second end cap 106. The blood processing apparatus 100 includes a blood inlet 108 and a blood outlet 110. A gas inlet 112 permits oxygen to be provided to the gas exchanger portion while a gas outlet 114 permits gases to exit the blood processing apparatus 100.

The blood processing apparatus 100 includes a heat exchanger core 116, a heat exchanger element 118 disposed about the heat exchanger core 116, a cylindrical shell 120 disposed about the heat exchanger element 118 and a gas exchanger element 122, all disposed inside the outer shell or housing 102. The heat exchanger element 118 and the gas exchanger element 122 may each include a number of hollow fibers as discussed with respect to the blood processing apparatus 50. In some embodiments, the housing 102 includes an annular portion 124 that is in fluid communication with the blood outlet 110.

In use, blood enters the blood processing apparatus 100 through the blood inlet 108 and passes into the heat exchanger core 116. The blood fills the heat exchanger core 116 and exits through an elongate core aperture 126 and thus enters the heat exchanger element 118. In some embodiments, the heat exchanger core 116 includes a single elongate core aperture 126 while in other embodiments the heat exchanger core 116 may include two or more elongate core apertures 126. In some embodiments, the elongate aperture 126 allows or directs blood to flow through the heat exchanger element 118 in a circumferential direction.

As shown in FIG. 6, according to some embodiments, the cylindrical shell 120 includes an elongate collector or channel 127. The channel 127 may be disposed at a location substantially diametrically opposed to the location of the elongate core aperture 126. Locating the channel 127 substantially opposite the location of the core aperture 126 causes blood to flow in a generally circumferential flow pattern within the heat exchanger element 118. The channel 127 may extend from between about 1 and about 15 degrees about the circumference of the cylindrical shell 120. In one exemplary embodiment, the channel 127 extends about 5 degrees about the circumference.

After blood passes through the heat exchanger element 118, it collects in the channel 127 and flows into an annular shell aperture 128. The shell aperture 128, in various embodiments, extends entirely or substantially around the circumference of the cylindrical shell 120, such that blood exits the inner cylindrical shell 120 around the entire or substantially the entire circumference of the shell 120. In some embodiments, the radially disposed shell aperture 128 may be located near an end of the blood processing apparatus 100 that is opposite the blood outlet 110, thereby causing the blood to flow through the gas exchanger element 122 in a longitudinal direction. Blood then collects in the annular portion 124 before exiting the blood processing apparatus 100 through the blood outlet 110.

Figure 7:
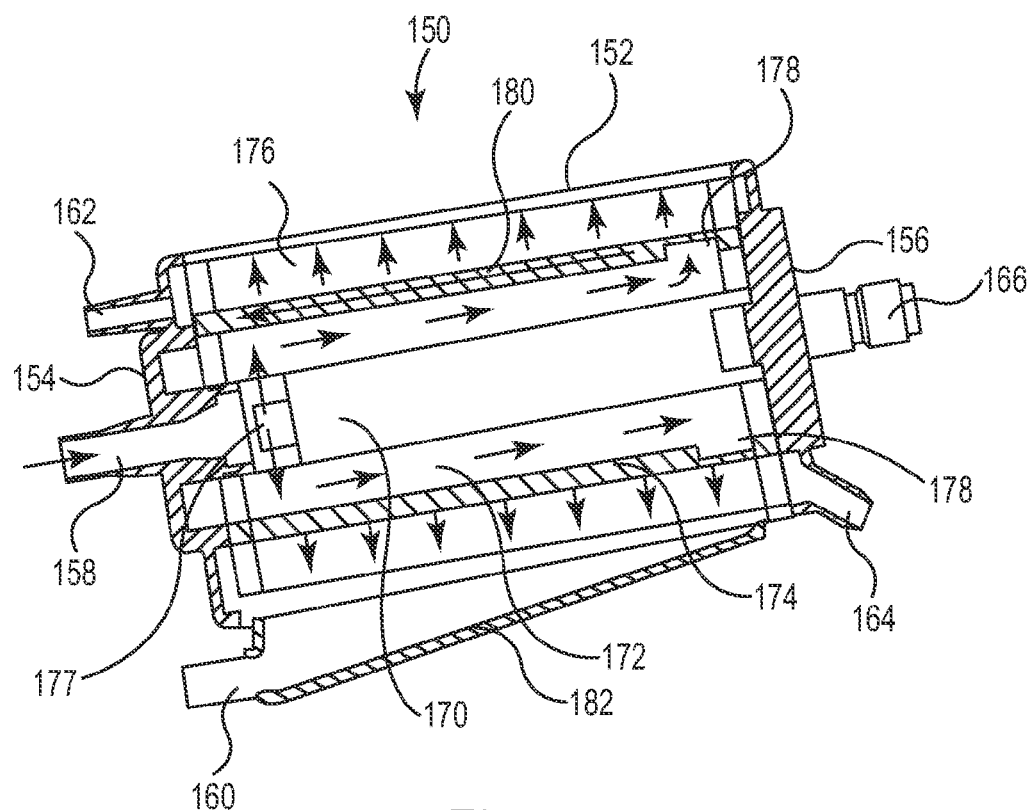
FIG. 7 is a cross-sectional view of an embodiment of a blood processing apparatus in accordance with an embodiment of the invention.

FIG. 7 is a cross-sectional view of a blood processing apparatus 150 in which blood flow through the heat exchanger portion is longitudinal while blood flow through the gas exchanger portion is either radial or circumferential. The blood processing apparatus 150 includes a housing 152, a first end cap 154 and a second end cap 156. The blood processing apparatus 150 includes a blood inlet 158 and a blood outlet 160. A gas inlet 162 permits oxygen to be provided to the gas exchanger portion while a gas outlet 164 permits gases to exit the blood processing apparatus 150.

The blood processing apparatus 150 includes a heat exchanger core 170, a heat exchanger element 172 disposed about the heat exchanger core 170, a cylindrical shell 174 disposed about the heat exchanger element 172 and a gas exchanger element 176 disposed about the cylindrical shell 174. The heat exchanger element 172 and the gas exchanger element 176 may each include a number of hollow fibers as discussed above with respect to the blood processing apparatus 50.

In use, blood enters through the blood inlet 158 and passes partially into the heat exchanger core 170 before exiting through a core aperture 177. Blood flows through the core aperture 177 and enters the heat exchanger element 172. In some embodiments, the heat exchanger core 170 includes a single core aperture 177 while in other embodiments the heat exchanger core 170 may include two or more core apertures 177. The core aperture 177 may extend partially or entirely around the circumference of heat exchanger core 170. The blood enters the heat exchanger element 172 at a first end near the blood inlet 158. The blood then flows longitudinally through the heat exchanger element 172 and exits through a radially disposed shell aperture 178 in the cylindrical shell 174. In some embodiments, the radially disposed shell aperture 178 is located at a second end that is opposite the first end, thereby causing the blood to flow in a longitudinal direction through the heat exchanger element 172.

After blood passes through the heat exchanger element 172, the blood exits the inner cylindrical shell 174 through the radially disposed shell aperture 178 and enters an elongate collector 180 that is disposed between the cylindrical shell 174 and the gas exchanger element 176. In some embodiments, the collector 180 is formed in the cylindrical shell 174. In some embodiments, the elongate collector 180 is configured to permit blood exiting the elongate collector 180 and entering the gas exchanger element 176 to flow in a circumferential direction. For example, the elongate collector 180 may include an elongate channel or may include one or more apertures disposed longitudinally along the gas exchanger element 176. In these embodiments, the blood flow exits at one circumferential location, such that blood flows through the gas exchanger element along a generally cylindrical flow path. According to other embodiments, the elongate collector 180 includes a plurality or channel or apertures disposed at various locations about the circumference of the elongate collector, such that blood flows through the gas exchanger element 176 in a generally radial direction. Blood exiting the gas exchanger element 176 passes into a tapered portion 182 that directs the blood through the blood outlet 160.

Figure 8:
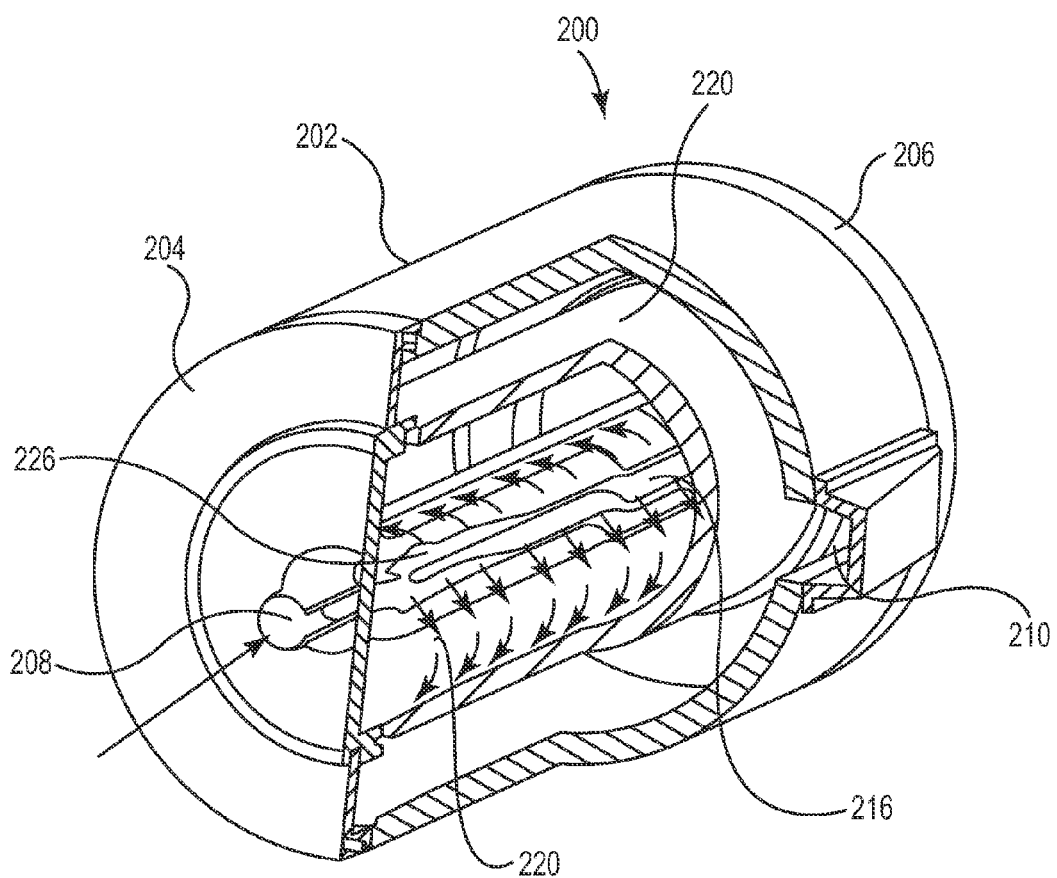
FIG. 8 is a partial cross-sectional perspective view of an embodiment of a blood processing apparatus in accordance with an embodiment of the invention.
Figure 9:
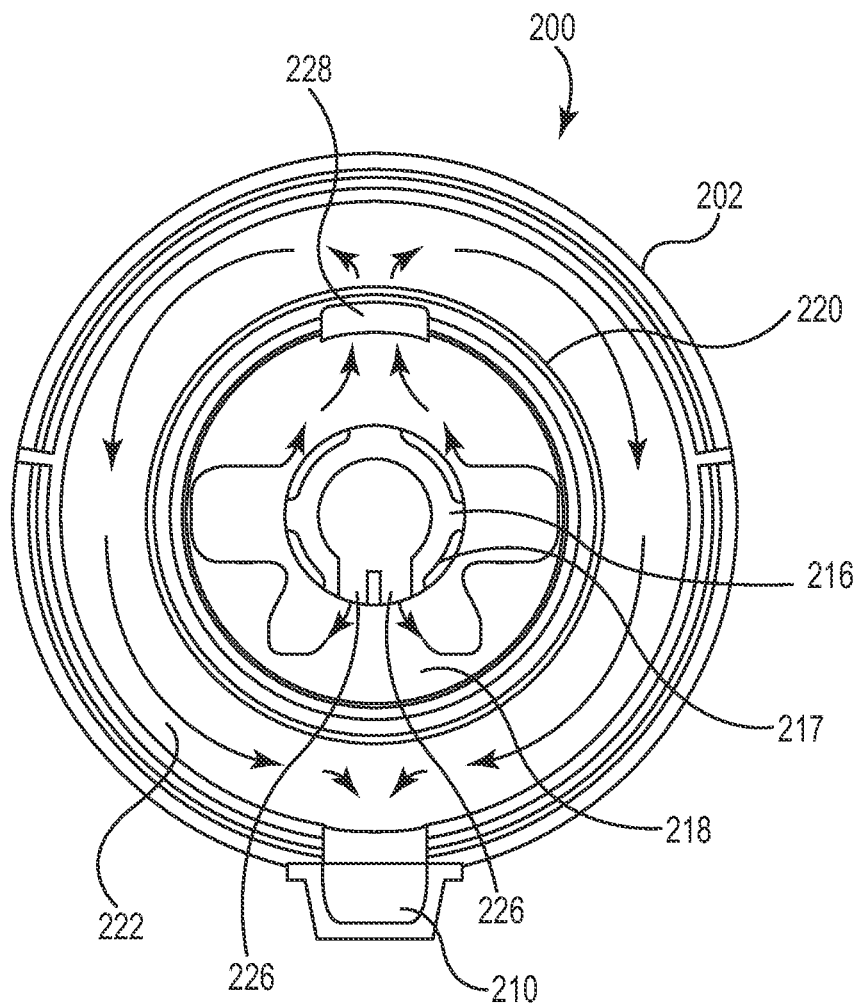
FIG. 9 is a cross-sectional view of an embodiment of a blood processing apparatus in accordance with an embodiment of the invention.
Figure 10:
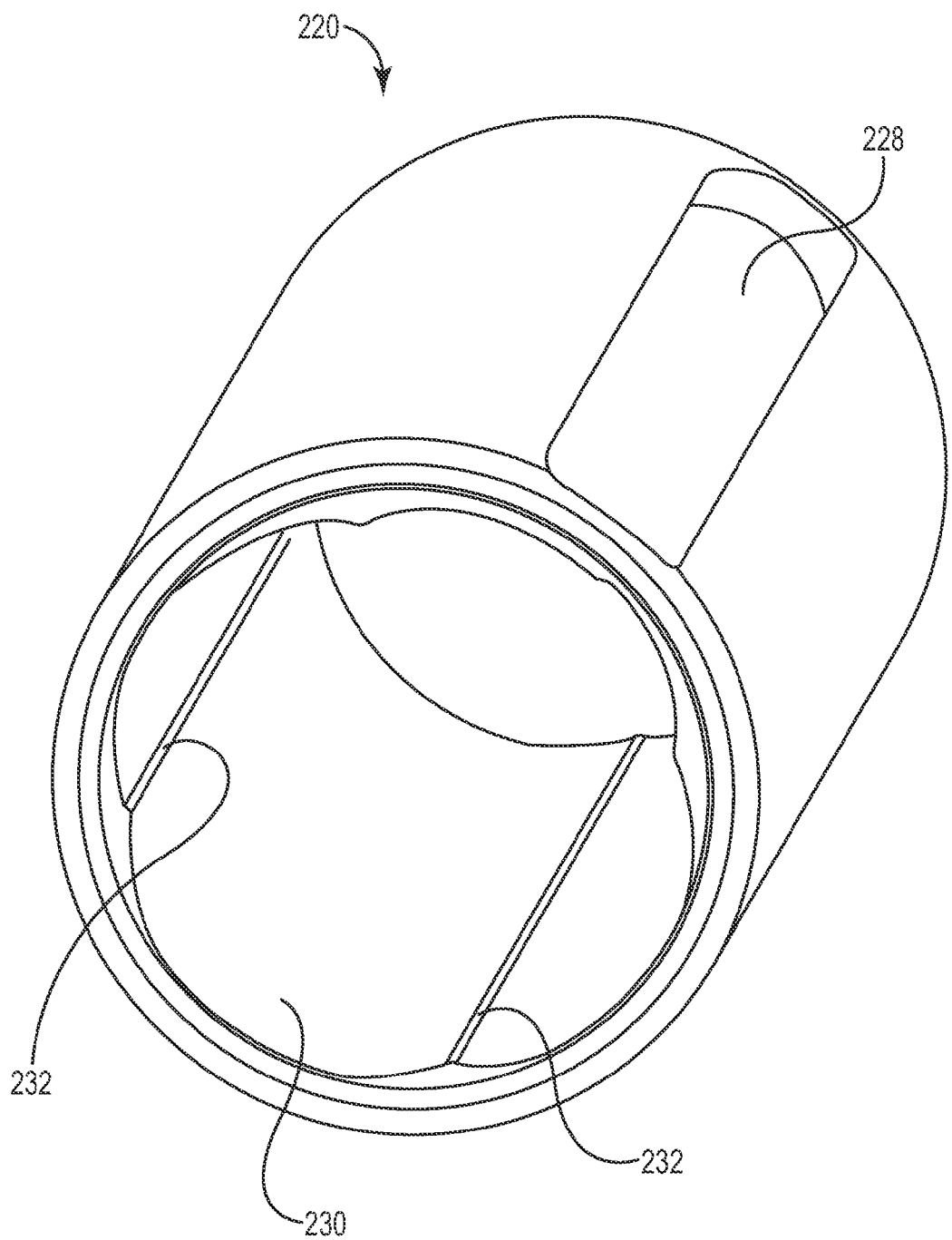
FIGS. 10 and 11 are perspective views of portions of the blood processing apparatus of FIG. 8.

FIGS. 8-10 show various views of a blood processing apparatus 200 where blood flow through the heat exchanger portion is both circumferential and radial, while blood flow through the gas exchanger portion is circumferential. As shown, the blood processing apparatus 200 includes a housing 202, a first end cap 204 and a second end cap 206. The blood processing apparatus 200 includes a blood inlet 208 and a blood outlet 210. The blood processing apparatus 200 includes a core 216, a heat exchanger element 218 disposed about the core 216, a cylindrical shell 220 disposed about the heat exchanger element 218, and a gas exchanger element 222 disposed about the cylindrical shell 220. The heat exchanger element 218 and the gas exchanger element 222 may each include a number of hollow fibers as discussed above with respect to the blood processing apparatus 50.

In use, blood enters through the blood inlet 208 and passes into the core 216. The blood fills the core 216 and exits through a series of core apertures 226. As shown in FIG. 8, the apertures are arranged to form a first elongate row and a second elongate row, with each row generally parallel to and in close proximity to the other row. In other embodiments, the core 216 includes a first elongate channel and a second elongate channel, with each channel generally parallel to and in close proximity to the other channel. In some embodiments, the elongate core apertures 226 permit blood to flow through the heat exchanger element 118 in a circumferential direction. In exemplary embodiments, the core apertures 226 are configured such that blood exiting the core 216 will flow through each of the first and second rows or channels, with blood exiting the first row or channel deflected or directed in a first circumferential direction and blood exiting the second row or channel deflected or directed in a second circumferential direction. In this configuration, blood flow thus exits the core and flows in a circumferential fashion through the heat exchanger element 218, with some blood flowing in one direction and some blood flowing in an opposite direction.

FIG. 10 is a perspective view of the cylindrical shell 220 according to various exemplary embodiments. As shown, the cylindrical shell 220 includes an inner surface 230. In some embodiments, as illustrated, one or more elongate shell ribs or lobes 232 may be disposed on the inner surface 230 and may be configured to cause at least some of the blood flowing past the one or more shell ribs or lobes 232 to demonstrate a modified circumferential flow, which includes a radial flow component. According to various embodiments, the inner surface 230 of the cylindrical shell 220 may have between two and eight distinct lobes 232, and in one embodiment the inner surface 230 has four lobes 232. In various embodiments, the lobes 232 are formed by adding additional material the inner surface, such that the internal diameter of the cylindrical shell 220, at the point where one lobe meets another lobe, is reduced by between about 5 and about 20 percent. In other embodiments, the lobes 232 are formed by removing material from the inner surface 230 or by some combination of adding and removing material.

In use, as blood flows through the heat exchanger element 218 in a circumferential manner, as described above, the blood will contact the lobes 232, which will in turn impart a radial flow component on the blood. In other words, the blood will then be flowing through the heat exchanger element 218 with an overall flow configuration that includes both a circumferential flow component and a radial flow component. The arrows shown in the heat exchanger element 218 in FIG. 9 represent the blood flow pattern caused by the lobes 232, according to this exemplary embodiment.

According to various embodiments, the core 216 includes exterior channels 217. As shown in FIG. 9, the core 216 includes four channels 217. In various embodiments, the channels are configures to further enhance the radial flow component of the blood. In various embodiments, the channels 217 are disposed at a location on the perimeter of the core 216 that is configured to cooperate with the lobes 232 formed in the inside surface of the cylindrical shell 220. For example, the channels 217 and lobes 232 may be circumferentially offset from one another such that blood is deflected radially inward by the lobes 232, simultaneous continued to move in the circumferential flow pattern, then is deflected radially outward by the channels 217. This configuration may then continue around the entire circumference of the core 216. In this manner, the combined radial and circumferential flow pattern of blood within the heat exchanger element 218 may be enhanced.

Figure 11:
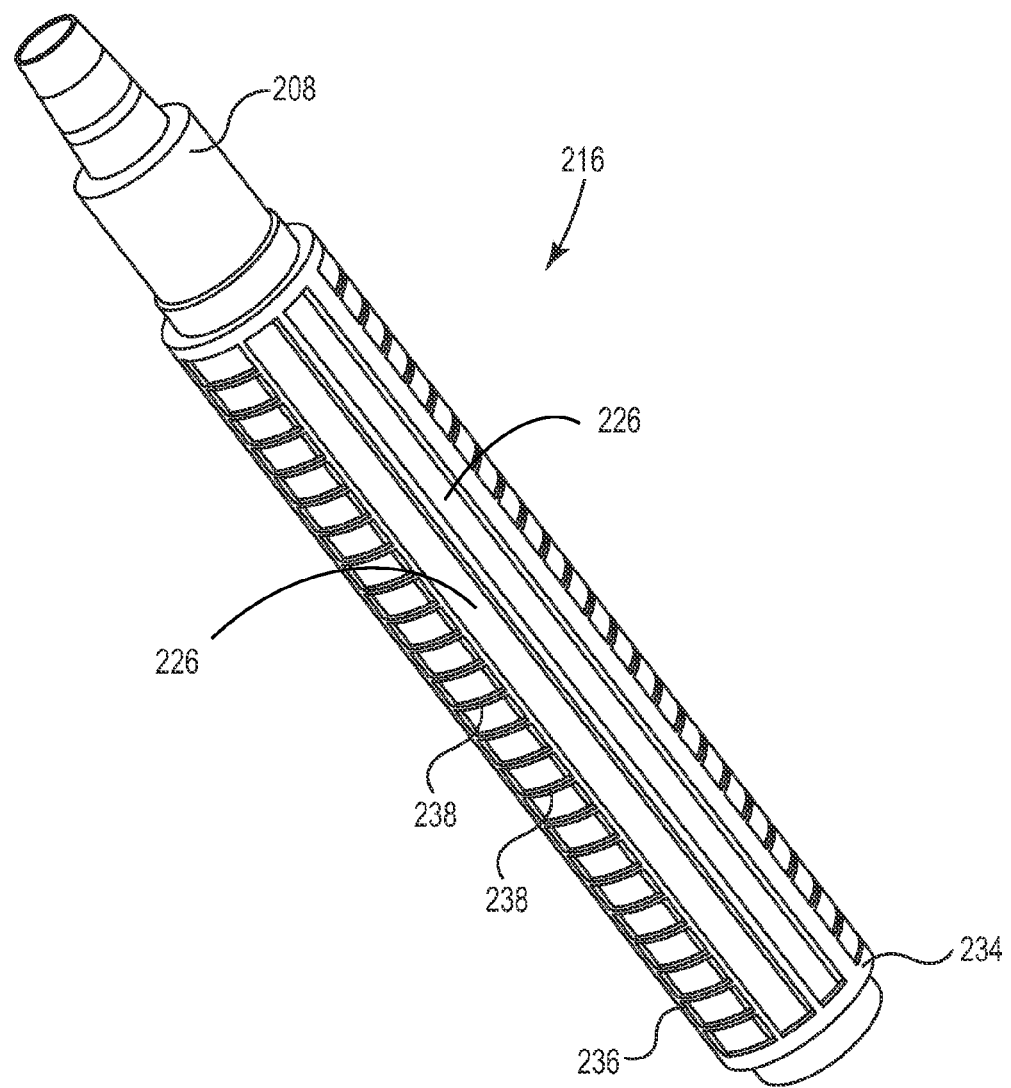

FIG. 11 is a perspective view of the heat exchanger core 216. The heat exchanger core 216 has an outer surface 234. In some embodiments, as illustrated, one or more elongate core ribs 236 may be disposed on the inner surface 234 and may be configured to cause at least some of the blood flowing past the one or more elongate core ribs 236 to demonstrate a modified circumferential flow (e.g., to have both a circumferential and a radial flow component). In some embodiments, the outer surface 234 may include a plurality of transverse ribs 238. In some embodiments, the radially disposed ribs 238 extend radially outward from the core 216 to provide a space between the heat exchanger core 216 and the hollow fibers wrapped about the core 216. This space enhances blood flow around the fibers, which enhances heat transfer and reduces pressure drop in the heat exchanger. According to some embodiments, the ribs are disposed along substantially the entire effective length of the heat exchanger core 216. The ribs may be disposed generally transverse to a longitudinal axis of the core 216.

After blood passes through the heat exchanger element 218, the blood exits the cylindrical shell 220 through an elongate shell aperture 228. In some embodiments, the elongate shell aperture 228 may be diametrically opposed from the elongate core aperture 226, thereby causing blood to flow in a circumferential direction. The blood enters the gas exchange element 222 and passes circumferentially towards the blood outlet 210.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

We claim:

1. A blood processing apparatus comprising:
   a housing having a blood inlet and a blood outlet, the blood inlet extending into an interior of the housing;
   a core arranged coaxially within the housing, the core having a core interior in fluid communication with the blood inlet, the core including an outer surface and only a single elongate core aperture formed within the outer surface and extending generally parallel to a core longitudinal axis, the elongate core aperture configured to permit blood to exit from the core interior such that all blood exiting the core interior exits through the elongate core aperture;
   heat exchanger hollow fibers disposed about the core such that a heat exchanger fluid may flow through the heat exchanger hollow fibers and blood passing from the elongate core aperture may flow across the heat exchanger hollow fibers;
   a cylindrical shell arranged coaxially about the heat exchanger hollow fibers, the cylindrical shell including an elongate shell aperture configured to permit blood to exit from the cylindrical shell such that all blood exiting the cylindrical shell exits through the elongate shell aperture; and
   gas exchanger hollow fibers disposed about the inner cylindrical shell such that gases may flow through the gas exchange hollow fibers and blood passing from the elongate shell aperture may flow across the gas exchanger hollow fibers and towards the blood outlet;
   wherein the shell aperture is disposed at a location substantially diametrically opposite the location of the core aperture, such that blood flows across the heat exchanger hollow fibers is substantially circumferential wherein the blood outlet is disposed at a location diametrically opposite the location of the shell aperture, such that blood passing from the shell aperture to the blood outlet is substantially circumferential.

2. The blood processing apparatus of claim 1, wherein the cylindrical shell further includes a plurality of lobes configured to impart a radial flow component to the blood.

3. The blood processing apparatus of claim 2, further comprising an elongate collection space disposed between the gas exchanger hollow fibers and the housing, the collection space diametrically opposed to the elongate shell aperture and in fluid communication with the blood outlet.

4. The blood processing apparatus of claim 1, wherein the shell aperture comprises a radially disposed aperture near an end of the cylindrical shell opposite that of the blood inlet such that blood exiting the radially disposed aperture flows over the gas exchanger hollow fibers in a longitudinal direction.

5. The blood processing apparatus of claim 1, wherein the housing defines an annular space configured to collect blood passing over the gas exchanger hollow fibers and direct the blood towards the blood outlet.

6. The blood processing apparatus of claim 1, wherein the outer surface of the core comprises a plurality of longitudinally extending core ribs that are configured to impart a radial component to blood flow around the heat exchanger core.

7. The blood processing apparatus of claim 6, wherein the cylindrical shell has an inner surface and a plurality of longitudinally extending shell ribs on the inner surface of the cylindrical shell that are configured to impart a radial component to blood flow around the core.

8. The blood processing apparatus of claim 6, wherein the outer surface of the heat exchanger core further comprises a plurality of transverse ribs that are configured to provide a space between the heat exchanger core and the heat exchanger hollow fibers.

9. The blood processing apparatus of claim 1, wherein the cylindrical shell comprises an elongate shell aperture disposed diametrically opposed to the pair of elongate core apertures.

10. A blood processing apparatus comprising:
an outer housing having a blood inlet and a blood outlet;
a heat exchanger core arranged within the housing and having a core interior in fluid communication with the blood inlet, the heat exchanger core including an outer surface and only a single elongate core channel formed through the outer surface such that blood may exit from the core interior with a generally circumferential flow configuration such that all blood exiting the heat exchanger core interior exits through the elongate core channel;
heat exchanger hollow fibers disposed about the heat exchanger core such that a heat exchanger fluid may flow through the heat exchanger hollow fibers and blood exiting from the core channel may flow across the heat exchanger hollow fibers;
a cylindrical shell arranged coaxially about the heat exchanger hollow fibers, the cylindrical shell including an elongate shell channel formed within an inner surface of the shell, at a circumferential location generally opposite a location of the elongate core channel, and a radially disposed shell aperture disposed near an end opposite the blood outlet, wherein the elongate shell channel and the shell aperture are in fluid communication, such that blood passing over the heat exchanger hollow fibers flows into the elongate shell channel and exits the cylindrical shell through the shell aperture such that all blood exiting the cylindrical shell exits through the radial shell aperture;
gas exchanger hollow fibers disposed about the cylindrical shell such that gases may flow through the gas exchange hollow fibers and blood passing from the cylindrical shell may flow across the gas exchanger hollow fibers towards the blood outlet in a longitudinal flow path.

11. The blood processing apparatus of claim 10, wherein the inner surface of the cylindrical shell further includes a plurality of lobes configured to impart a radial flow component to the blood.

12. The blood processing apparatus of claim 10, wherein the outer surface of the core comprises a plurality of longitudinally extending core ribs that are configured to impart a radial component to blood flow around the heat exchanger core.

13. The blood processing apparatus of claim 12, wherein the cylindrical shell has an inner surface and a plurality of longitudinally extending shell ribs on the inner surface of the cylindrical shell that are configured to impart a radial component to blood flow around the core.

* * * * *